US012642937B2

(12) United States Patent　　　　(10) Patent No.:　US 12,642,937 B2
Yu et al.　　　　　　　　　　　　　　(45) Date of Patent:　　　Jun. 2, 2026

(54) FLEXIBLE SMELL GENERATING DEVICE AND METHODS FOR USE THEREOF

(71) Applicant: City University of Hong Kong, Hong Kong (CN)

(72) Inventors: Xinge Yu, Hong Kong (CN); Yiming Liu, Hong Kong (CN); Chun Ki Yiu, Hong Kong (CN); Rui Shi, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 1081 days.

(21) Appl. No.: 17/655,417

(22) Filed: Mar. 18, 2022

(65) Prior Publication Data

US 2023/0293845 A1　　Sep. 21, 2023

(51) Int. Cl.
A61M 21/02　　　(2006.01)
A61M 21/00　　　(2006.01)
G06F 3/01　　　　(2006.01)

(52) U.S. Cl.
CPC ............. A61M 21/02 (2013.01); G06F 3/011 (2013.01); *A61M 2021/0016* (2013.01); *A61M 2021/0066* (2013.01); *A61M 2205/3368* (2013.01); *A61M 2205/3606* (2013.01); *A61M 2205/364* (2013.01); *A61M 2205/3673* (2013.01)

(58) Field of Classification Search
CPC .......... A61M 21/02; A61M 2021/0016; A61M 2021/0066; A61M 2205/3368; A61M 2205/3606; A61M 2205/364; A61M 2205/3673; G06F 3/011; A61L 9/03; A61L 9/035
See application file for complete search history.

(56) References Cited

U.S. PATENT DOCUMENTS 6,024,717 A * 2/2000 Ball .................. A61M 37/0092
　　　　　　　　　　　　　　　　　604/500
7,023,304 B2 * 4/2006 Shen ...................... G02B 26/08
　　　　　　　　　　　　　　　　　335/78

(Continued)

FOREIGN PATENT DOCUMENTS

WO　　WO-2016057336 A1 * 4/2016 ............... A61L 9/04
WO　　WO-2019207298 A1 * 10/2019 ............. G06Q 10/00

OTHER PUBLICATIONS

Wu, Y., Du, X., Li, Y., Tai, H., & Su, Y. (2018). Optimization of temperature uniformity of a serpentine thin film heater by a two-dimensional approach. Microsystem Technologies, 25(1), 69-82. doi:10.1007/s00542-018-3932-0 (Year: 2018).*

(Continued)

*Primary Examiner* — Carrie R Dorna
*Assistant Examiner* — Julie Thi Tran
(74) *Attorney, Agent, or Firm* — S&F/WEHRW

(57)　　　　　　ABSTRACT

The present invention provides a thermo-controlled smell generating device with an active cooling mechanism to allow a user thereof to control on/off of the device in a relatively short response time absent any temperature fluctuations even after a significant number of heating and cooling cycles. The present invention is ideal for generating olfaction in highly interactive or fast-changing environments such as virtual immersive environments.

14 Claims, 28 Drawing Sheets
(26 of 28 Drawing Sheet(s) Filed in Color)

(56) References Cited

U.S. PATENT DOCUMENTS

| | | | |
|---|---|---|---|
| 2002/0021860 A1* | 2/2002 | Ruan | H01H 50/005 |
| | | | 385/18 |
| 2004/0040828 A1* | 3/2004 | Ivanciw | H01H 47/04 |
| | | | 200/600 |
| 2006/0029653 A1* | 2/2006 | Cronk | A61M 15/085 |
| | | | 128/200.24 |
| 2007/0051826 A1* | 3/2007 | Schofield | A61L 9/03 |
| | | | 239/57 |
| 2007/0057752 A1* | 3/2007 | Wang | H01H 37/58 |
| | | | 335/37 |
| 2009/0108094 A1* | 4/2009 | Ivri | A61L 9/14 |
| | | | 239/101 |
| 2013/0239690 A1* | 9/2013 | Tadano | G01R 33/56358 |
| | | | 73/644 |
| 2015/0048178 A1* | 2/2015 | Edwards | G06F 3/011 |
| | | | 239/128 |
| 2016/0178251 A1* | 6/2016 | Johnson | A61F 7/02 |
| | | | 62/3.5 |
| 2016/0361494 A1* | 12/2016 | Jürg | A61M 5/172 |
| 2018/0280708 A1* | 10/2018 | Escalona | H02J 50/10 |
| 2018/0286351 A1* | 10/2018 | Fateh | A61K 9/007 |
| 2019/0224445 A1* | 7/2019 | Fernandes | A61B 5/4815 |
| 2021/0346562 A1* | 11/2021 | Obrist | A61L 9/035 |

OTHER PUBLICATIONS

Yang, Y., Li, S., Xu, H., Xu, Y., & Chen, Y. (Feb. 2022). Fabrication of flexible microheater with tunable heating capabilities by direct laser writing and selective electrodeposition. Journal of Manufacturing Processes, 74, 88â99. doi:10.1016/j.jmapro.2021.11.045 (Year: 2022).*

Saxena, A., & Agrawal, V. K. (2017). Comparative study of cantilever RF MEMS switch. Materials Today: Proceedings, 4(9), 10328â10331. doi:10.1016/j.matpr.2017.06.374 (Year: 2017).*

Pyralux® Fr Copper Clad Laminate, coverlay, bondply & sheet adhesive. (2021). Retrieved from https://www.dupont.com/electronics-industrial/pyralux-fr.html#:~:text=DuPont%E2%84%A2%20Pyralux%C2%AE%20FR%20coverlay%20(bondply)%20composites%20are%20constructed,Certified%20to%20IPC%204203A/1 (Year: 2021).*

Komori, T., et al., Effects of citrus fragrance on immune function and depressive states. Neuroimmunomodulation, 1995. 2(3): p. 174-80.

Lehrer, J., et al., Ambient odor of orange in a dental office reduces anxiety and improves mood in female patients. Physiol Behav, 2000. 71(1-2): p. 83-6.

Lehrer, J., et al., Ambient odors of orange and lavender reduce anxiety and improve mood in a dental office. Physiol Behav, 2005. 86(1-2): p. 92-5.

Sano, K., et al., Concentration Effects of Green Odor on Event-related Potential (P300) and Pleasantness. Chemical Senses, 2002. 27(3): p. 225-230.

Kato, S. and T. Nakamoto, Olfactory Display Based on Sniffing Action. 2018 IEEE Conference on Virtual Reality and BD User Interfaces (VR), 2018: p. 597-598.

Radvansky, B.A. and D.A. Dombeck, An olfactory virtual reality system for mice. Nature Communications, 2018. 9(1): p. 839.

Yamada, T., et al. Wearable olfactory display: Using odor in outdoor environment. in IEEE Virtual Reality Conference (VR 2006). 2006. IEEE.

Kim, D.W. and H. Ando. Development of directional olfactory display. in Proceedings of the 9th ACM SIGGRAPH Conference on Virtual-Reality Continuum and its Applications in Industry. 2010.

Nambu, A., et al. Visual-olfactory display using olfactory sensory map. in 2010 IEEE Virtual Reality Conference (VR). 2010. IEEE.

Yanagida, Y., et al., A nose-tracked, personal olfactory display, in ACM SIGGRAPH 2003 Sketches & Applications. 2003. p. 1-1.

Matsukura, H., T. Yoneda, and H. Ishida, Smelling Screen: Development and Evaluation of an Olfactory Display System for Presenting a Virtual Odor Source. IEEE Transactions on Visualization and Computer Graphics, 2013. 19: p. 606-615.

Yanagida, Y., et al., An unencumbering, localized olfactory display. CHI '03 Extended Abstracts on Human Factors in Computing Systems, 2003.

Micaroni, L., et al., An Olfactory Display to Study the Integration of Vision and Olfaction in a Virtual Reality Environment. Journal of Computing and Information Science in Engineering, 2019. 19(3).

Wearables—Worldwide | Satista Market Forecast. 2020; Available from: https://www.statista.com/outlook/dmo/eservices/fitness/wearables/worldwide.

* cited by examiner 107
106
105
104
103
102
101
Skin

FLEXIBLE SMELL GENERATING DEVICE AND METHODS FOR USE THEREOF

TECHNICAL FIELD

The present invention relates to a flexible smell generating device and methods for using thereof.

BACKGROUND

There has been a number of wearable olfactory VR devices (e.g., Feelreal™, OVR Technology™, Vaqso™, etc.) available on the market, where most of them require replaceable cartridges with odorant capsules, liquid atomizers, and tiny fans to atomize perfume and blow out tiny perfume droplets. These olfactory VR devices are usually installed and mounted on visual VR devices as a supplement, but cannot be used independently. Additionally, they are neither stretchable nor flexible for direct contact with human skin. Furthermore, the bulkiness of the conventional olfactory VR devices affects the user's perception experience in immersive environments.

Olfactory display involves vaporizing odor from odorants in stock form and delivering to the human olfactory organ. The commonly used vaporization methods are natural evaporation, airflow, heating and atomization, and the commonly used odor delivery methods are natural diffusion, airflow, and tubes. Natural diffusion is combined with natural evaporation, heating, or airflow to create a spatially distributed odor from high concentration to low concentration. Fans combined with airflow vaporization and atomization (e.g., Kim and Ando, 2010; Matsukura et al., 2013) have been used to direct odors in the direction of the user's nose and control the duration of odor transmission. Tube method (e.g., Yamada et al., 2006; Yanagida et al. (1), 2003; Yanagida et al. (2), 2003; Micoaroni et al, 2019) involves a tube to deliver odor to the user's nose, which creates a closed system to better contact and control the odor flow. However, special care must be taken to prevent the previous odor from sticking to the inside of the tubes. As a result, one tube for each odor is usually used, which becomes cumbersome for users.

Although there are quite a number of studies in the field of olfactory VR devices, none of them appears to establish an independently operable device that can be easily used on human skin, thereby leading to a huge potential to develop an independent, easy-to-use and flexible smell generating device for immersive environments.

Therefore, a miniature, flexible smell generating device for use in a variety of fields including immersive environments and that eliminates or at least diminishes the disadvantages and problems described hereinbefore will be one of the objectives of the present invention.

SUMMARY OF THE INVENTION

Accordingly, the present invention provides a flexible smell generating device for use in a wide range of technical fields including, but not limited to, immersive environments (e.g., virtual reality, augmented reality, and mixed reality), wearable electronics, and olfactory-driven medical therapies. To minimize the size of and provide sufficient flexibility for the present device to be applied on human skin, the present smell generating device is preferably a multi-layered structure in the absence of any tube or liquid-delivery mechanisms. The activation mechanism of the present device is preferably by thermal stimulation to one or more thermally responsive elements within the present device.

In a first aspect, the present invention provides a flexible smell generating device for use on human skin.

In an exemplary embodiment, the present device includes a multi-layered structure. The multi-layered structure includes one or more smell generating modules, one or more active cooling elements, a plurality of electronic circuits, and a substrate, where each of the smell generating modules includes at least one open channel and at least one chamber containing at least one phase change material incorporating one or more of scent-releasing substance, odorants and inhalable content.

In certain embodiments, when the corresponding smell generating module is heated to a temperature at or above a melting temperature of the at least one phase change material, the scent, odors and/or inhalable content is/are released from the at least open channel to the surroundings, and when the corresponding smell generating module is cooled to a temperature below the melting temperature of the at least one phase change material, the at least one phase change material returns to solid state and the release of the scent, odors and/or inhalable content from the at least one open channel to the surroundings ceases; and where the one or more active cooling elements is/are controlled by the plurality of electronic circuits and configured to actively cool the corresponding smell generating module upon activation by the electronic circuits; and where the substrate is the most proximal layer of the multi-layered structure to the human skin and for securing the multi-layered structure to the human skin.

In certain embodiments, each of the smell generating modules further includes at least one heating element for heating the at least one phase change material, and at least one temperature sensing and control element for sensing and controlling temperature variations of the smell generating module during said heating.

In certain embodiments, the at least one heating element is a pair of electrodes.

In one embodiment, the pair of electrodes being the heating element is a pair of serpentine-shaped electrodes.

In one embodiment, the pair of electrodes can be made of a metal including, but not limited to, gold, chromium and copper.

In certain embodiments, the at least one temperature sensing and control element is a thermal sensitive resistor or thermistor.

In one embodiment, the thermistor is selected from a negative-temperature coefficient (NTC) thermistor.

In one embodiment, the thermistor has a beta value (B value) of approximately 4250K.

In certain embodiments, the at least one phase change material comprises paraffin wax.

In one embodiment, the phase change material has a melting temperature of about 50° C.

In certain embodiments, the smell generating module is configured to allow the phase change material be replaceable and incorporated with different scent or odor releasing elements from an initial phase change material.

In one embodiment, the initial phase change material can be replaced directly by heating the chamber of the smell generating module at a temperature above the melting temperature of the initial phase change material, followed by removing the molten phase change material from the chamber, which can protect the heating elements beneath. After that, the temperature of the chamber is maintained at the same temperature for melting a subsequent phase change material incorporated with the same or different scent or odor releasing elements from those in the initial phase change material. In this embodiment, no additional component is required to house the subsequent batch of phase change material to be replaced. Replacement can be done in a few simple steps.

In certain embodiments, the one or more active cooling elements is/are one or more electromagnetic actuators where each of them includes at least an electrically conductive coil and a magnet.

In certain embodiments, each of the smell generating module further includes at least a first polymer layer and a second polymer layer.

In certain embodiments, the first polymer layer includes a cavity while the second polymer layer includes a switch.

In certain embodiments, the magnet is disposed within the cavity on the first polymer layer while the at least one electrically conductive coil is attached to the switch.

In certain embodiments, the magnet is positioned within a magnetic field generated by the electrically conductive coil when an electric current is applied to the electrically conductive coil so as to generate an electromagnetic force to lift up the electrically conductive coil.

In one embodiment, the first polymer layer is made of polyethylene terephthalate (PET) and the cavity is defined by a polydimethylsiloxane (PDMS) ring disposed on said first polymer layer.

In one embodiment, the second polymer layer is made of polyimide (PI), and the switch is a cantilever.

In certain embodiments, the electronic circuits include a microcontroller unit (MCU) configured to control the switch of the at least one electrically conductive coil in order to adjust the oscillating frequency and amplitude of the electrically conductive coil.

In certain embodiments, the oscillating electrically conductive coil according to the electric current flowing through the coil acts as a mechanical actuator of the smell generating module.

In one embodiment, the mechanical actuator has a vibration frequency from 0 to about 10 Hz, and a vibration amplitude from 0 to about 1.86 mm.

In certain embodiments, the at least one electrically conductive coil is made of a metal including, but not limited to, copper, silver and gold.

In certain embodiments, the multi-layered structure of the present device further includes a plurality of electrical outputs where each of the electrical outputs communicates with the smell generating module individually to provide electric current at a switching frequency for the corresponding smell generating module.

In certain embodiments, the substrate is flexible and adhesive in order to secure the multi-layered structure to the human skin.

In certain embodiments, the electronic circuits are configured to be flexible and bendable for soldering electrical elements disposed under the electronic circuits and enabling the present device be applicable on human skin.

In certain embodiments, the one or more smell generating modules, the corresponding actuators, electronic circuits and electrical elements are disposed layer-by-layer on the flexible substrate that is to be in contact with human skin.

Other details and embodiments of the present device will be further described hereinafter.

A second aspect of the present invention provides an article including the present device described herein for providing olfaction and/or inhalable content to a user in need thereof. In certain embodiments, the article may include, but not limited to, a skin pad, patch, absorbent, and any layered structure applicable on human skin.

A third aspect of the present invention provides a method of using the present device or article described herein for providing olfaction and/or inhalable content to a user in immersive environments, where the immersive environments include, but not limited to, virtual reality (VR), augmented reality (AR) and mixed reality (MR). In an exemplary embodiment, the method includes: attaching the flexible smell generating device described herein on human skin; connecting the flexible smell generating device to a device of providing immersive environments to control the heating and active cooling elements of the smell generating device wirelessly; activating the heating element of the smell generating module to convert a phase change material from its solid state into molten state in order to release scent, odors and/or inhalable content initially incorporated with the phase change material, or activating the active cooling element of the smell generating module in order to cease the release of scent, odors and/or inhalable content.

Other aspects of the present invention include a method for using the present device or article in alleviating, preventing and/or treating diseases, symptoms and/or conditions in a subject in need thereof. The method includes attaching the present device described herein onto a skin of the subject to generate scent, odors or inhalable content with or without certain therapeutic agents released from the smell generating module. The present device can also be used in combination with any medical, motion-assistive, or rehabilitative device or system to provide an olfactory-driven therapies or therapeutic regime for a subject in need thereof. The subject of interest is mainly human, but may also include other animals. The diseases and/or conditions may include, but not limited to, any neurological, psychological, psychiatric, cancerous, chronic inflammatory, and immunodeficient or compromised diseases and/or conditions.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The patent or application file contains at least one drawing executed in color. Copies of this patent or patent application publication with color drawing(s) will be provided by the Office upon request and payment of the necessary fee.

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Figure 1A:
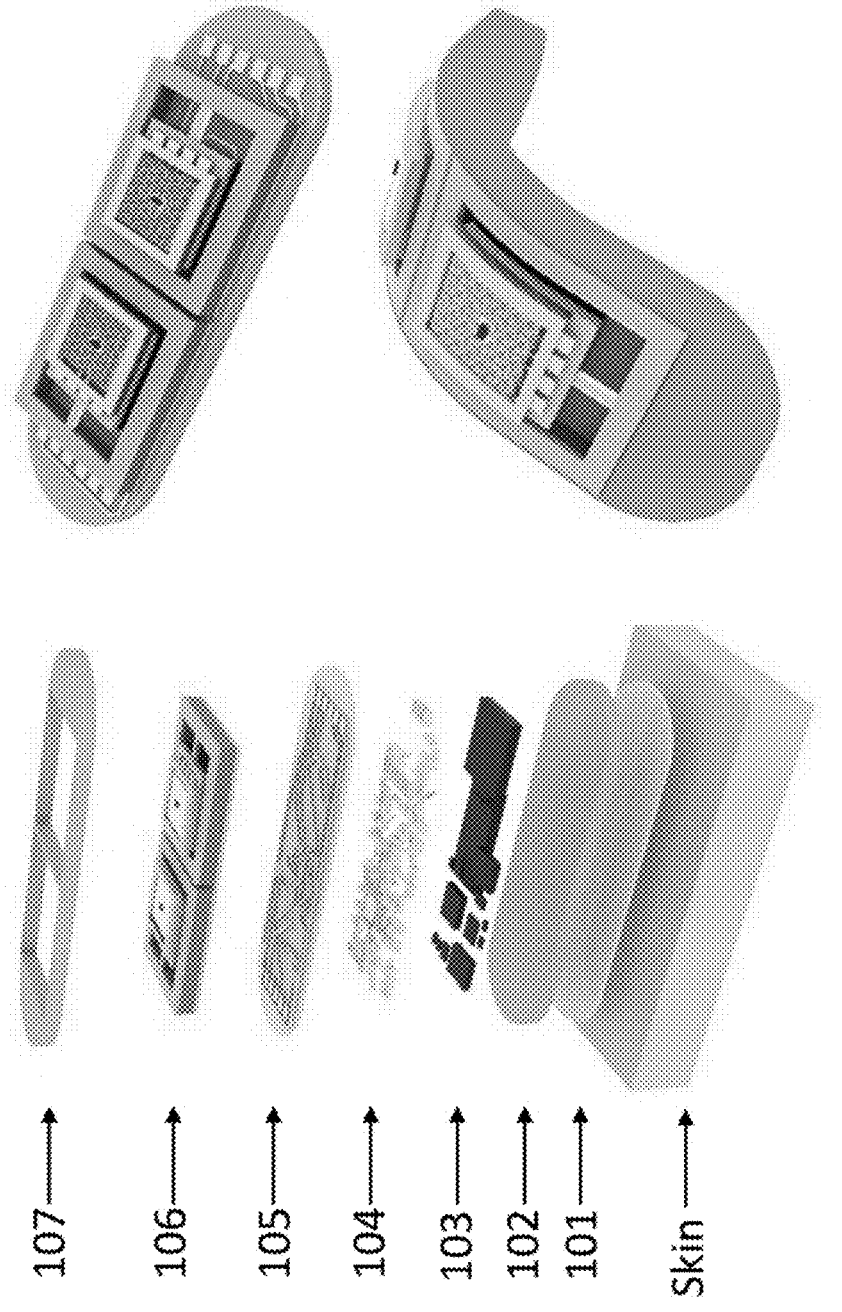
FIG. 1A schematically depicts the structure of the smell generating device according to an embodiment of the present invention.

In an exemplary embodiment, the present device is fabricated in a layer-by-layer configuration. An example of a multi-layered structure of the present device is depicted in FIG. 1A. In FIG. 1A, the most proximal layer to human skin surface is a bottom layer of polydimethylsiloxane (PDMS) 102 with an adhesive 101 to secure the present device on the human skin. A top layer of PDMS 107 is disposed on the smell generators 106 and configured to have openings corresponding to the positions and open channel of the smell generators 106. In this example, the two smell generators 106 are disposed side by side with each other. The two openings of the top layer of PDMS 107 allow the release of scents, odors, and/or inhalable content from the corresponding open channel of the smell generators to the surroundings. The flexible printed circuit board (FPCB) 105 is disposed under the smell generators 106 and on top of an electrode 104 and some electrical elements 103 to act as control mechanisms to provide heating and active cooling for the smell generators and for soldering electrical elements 103 disposed underneath. The electrical elements 103 are disposed on the bottom layer of PDMS 102. The electrical elements 103 include, but not limited to, a Bluetooth module, a microcontroller unit, capacitors, resistors, and a crystal oscillator.

Figure 1B:
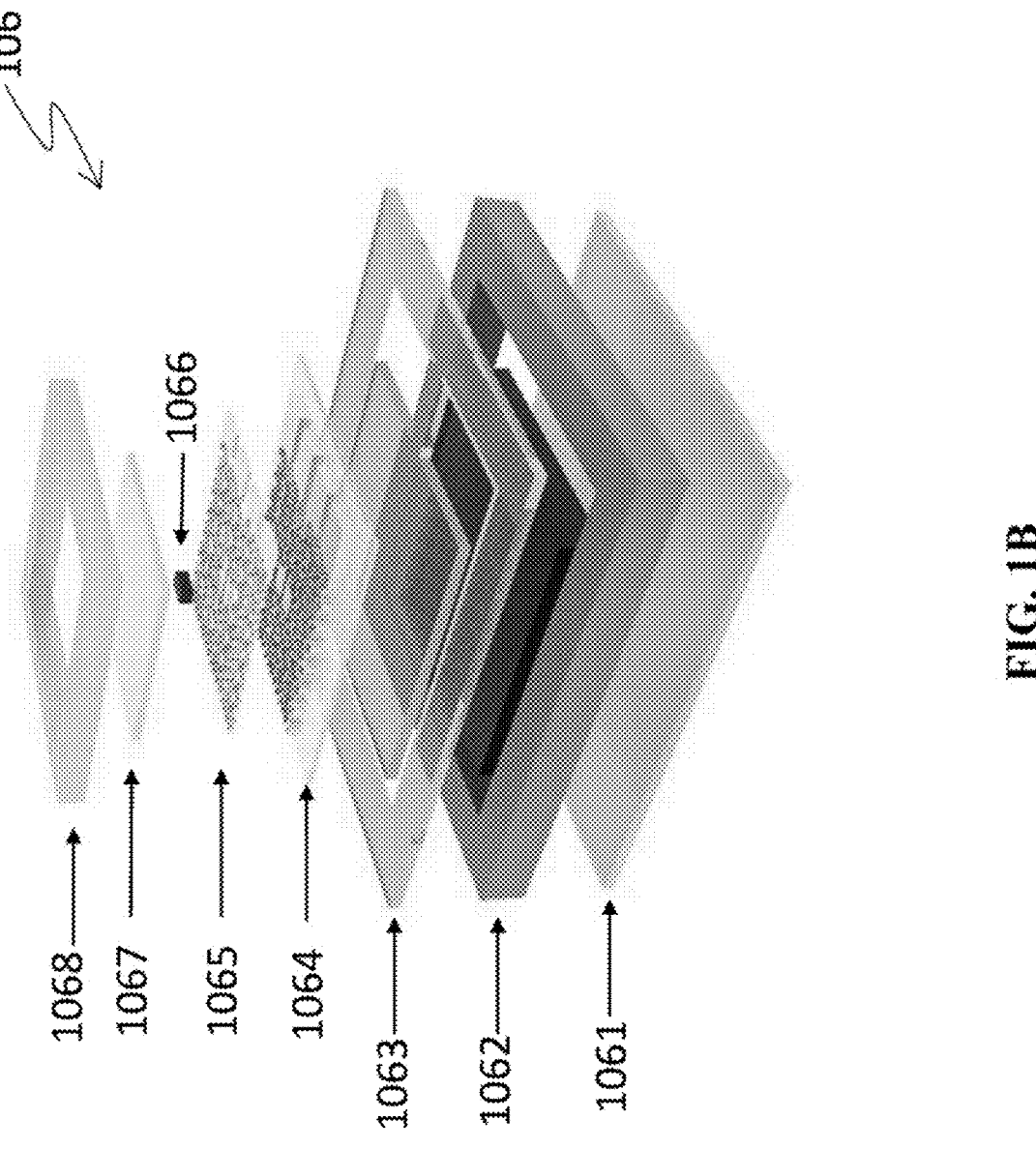
FIG. 1B schematically depicts the structure of the smell generating module according to an embodiment of the present invention.

FIG. 1B shows an exploded view of the smell generator 106. A thermo-controlled smell generating element and an electromagnetic-driven smell eliminating element are provided in the smell generator 106. A polyethylene terephthalate (PET) layer is used as a bottom layer 1061 to hold the upper structure. Stacking on the PET layer 1061, there is a magnet surrounded by a square hollow PDMS ring 1062. A PET layer with a cantilever 1063 is covered on the PDMS ring 1062 to guide the vibration of a conductive copper (Cu) coil when applied with a voltage. Thus, the Cu coil is attached to the cantilever while the magnet is disposed in a cavity defined by the PDMS ring 1062. A polyimide (PI) layer with serpentine-like gold (Au) electrodes 1064 is attached to the PET layer, serving as both heating channel and sensing channel. A negative-temperature coefficient (NTC) thermistor 1066 is inserted between the PI layer 1065 and paraffin layers 1067 to continuously monitor the temperature of the paraffin layers and control the heating channel's on/off states. Paraffin mixed with odorants forming paraffin layers 1067 are covered on the PI layer 1065 as the odorant storage chamber. When a voltage is applied to the serpentine-like Au electrodes 1064, the generated Joule heat could melt the paraffin to turn into molten state, and subsequently release the embedded odors. Finally, a hollow conductive Cu coil 1068 is placed around the paraffin layers and acts with the magnet as active cooling elements for the paraffin. Once an electric output to the Cu coil is powered off, the Cu coil 1068 falls due to gravity and contact with the cold magnet 1062, thereby changing the molten paraffin quickly into solid state and ceasing the release of odors accordingly.

Figure 1C:
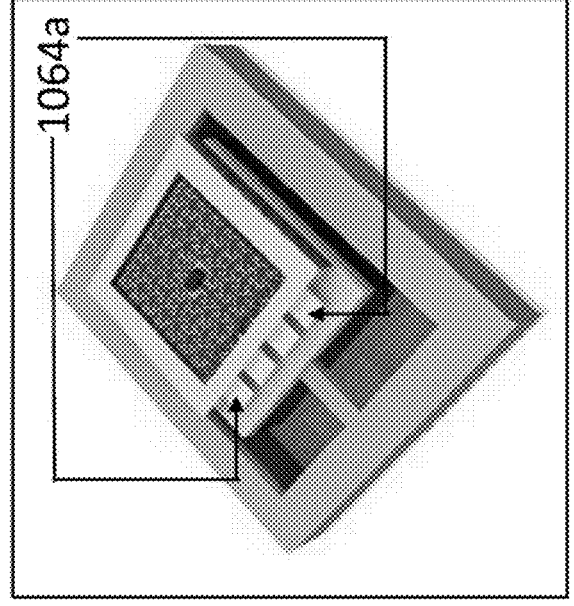
FIG. 1C is a perspective view of the smell generating module according to certain embodiments of the present invention.
Figure 1D:
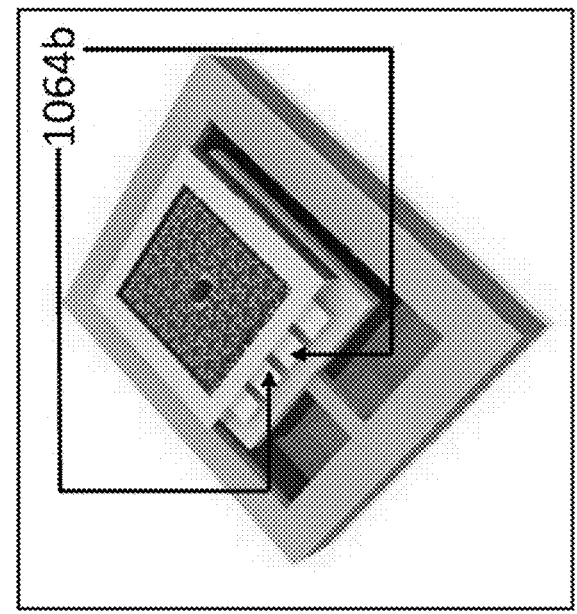
FIG. 1D shows an image of a prototype of the smell generating module according to an embodiment of the present invention.

FIGS. 1C and 1D depict two outer connectors 1064*a* being an interface of the heating element and two inner connectors 1064*b* being an interface of the sensing element as a three-dimensional schematic diagram and image from a prototype, respectively.

Figure 2A:
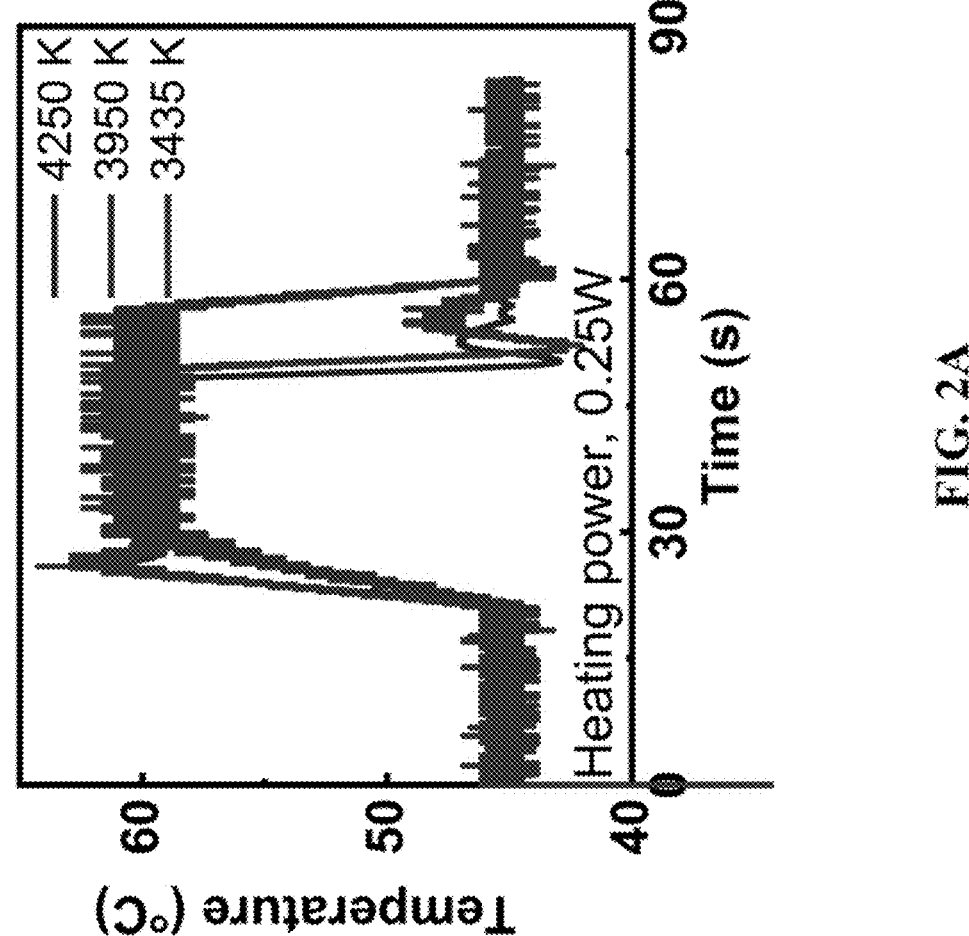
FIG. 2A shows the response performance of different thermistors in the smell generating module with different beta (b) values during heating and cooling cycles according to certain embodiments of the present invention.
Figure 2B:
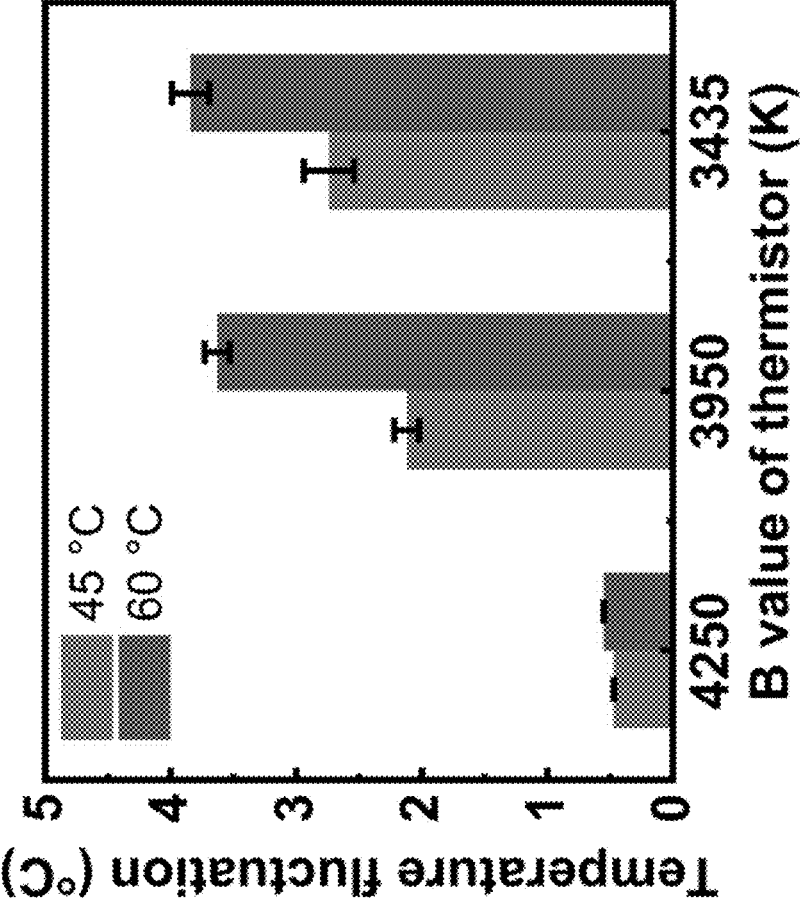
FIG. 2B shows the effect of different b values of the thermistors of the smell generating module on temperature variations during sensing according to certain embodiments of the present invention.

Turning to FIG. 2A, the thermal and electrical characteristics of the smell generating module is depicted. Three thermistors with different B values (4250K, 3950K, and 3435K) are subject to a heating and cooling cycle initially rising from 45° C. to 60° C. and return to 45° C. at a power of 0.25 W. Temperature change of each thermistor during the heating and cooling cycle was measured and the results are plotted as temperature curves as shown in FIG. 2A. It can be observed that the thermistor with the B value of 4250 K has the fastest response performance regarding the temperature variations among the three thermistors. Meanwhile, the temperature fluctuations of the corresponding thermistors with different B values were compared and the results are shown in FIG. 2B. From the results in FIG. 2B, the temperature of the thermistor with the B value of 4250 K fluctuated within 0.5° C., while that of the thermistor with the B value of 3950 K and 3435 K fluctuated between 2° C. and 5° C., showing that the higher the B value of the thermistor was, the less significant were the temperature fluctuations during the sensing.

Figure 2C:
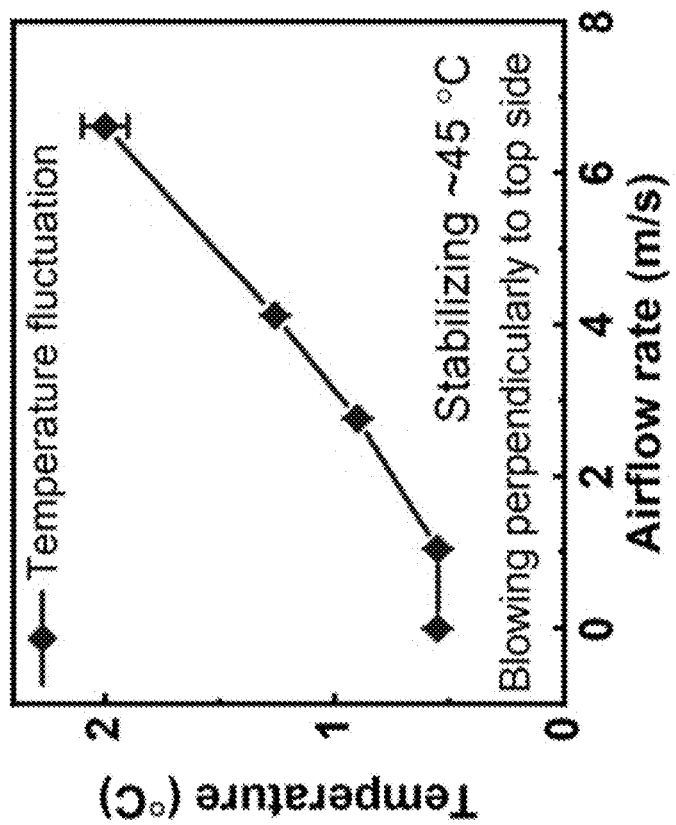
FIG. 2C shows the effect of different air flow rates on temperature variations of the thermistors of the smell generating module according to certain embodiments of the present invention.

Turning to FIG. 2C, the temperature change of the thermistor with the B value of 4250K when facing different airflow rates was measured to show the effect of the airflow on temperature fluctuation of the thermistor. When the air flows in a direction perpendicular to the upper side of the thermistor with a flow rate from 0 to approximately 6.3 m/s, the temperature began to fluctuate but less than 2° C. due to heat loss, which ensures that the air convection has little impact in the practical wearing process.

Figure 2D:
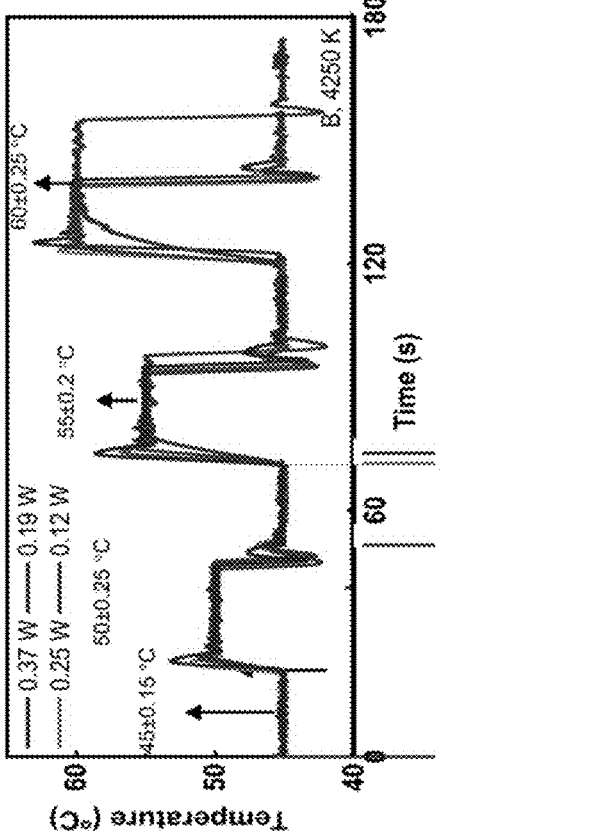
FIG. 2D shows the effect of different heating power levels on temperature variations of the thermistors of the smell generating module according to certain embodiments of the present invention according to certain embodiments of the present invention.

Turning to FIG. 2D, the temperature change of the thermistor with the B value of 4250K at different power levels (0.37 W, 0.25 W, 0.19 W, 0.17 W) was measured, and the corresponding temperature fluctuations are plotted as temperature curves shown in FIG. 2D. Stabilized temperatures of 45° C., 55° C., and 60° C. were measured with relatively minimal temperature fluctuations, where the lowest power (0.17 W) resulted in the slowest temperature response performance.

Figure 2E:
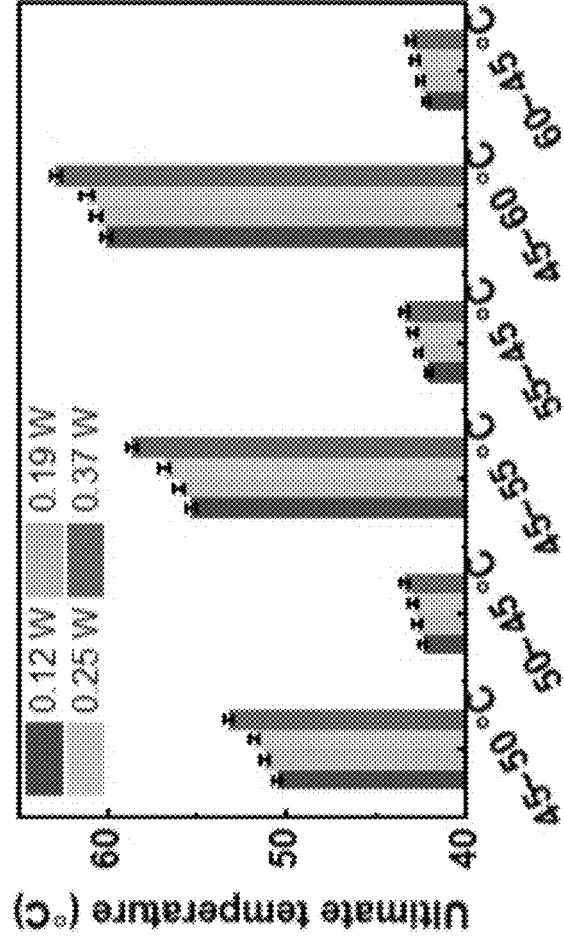
FIG. 2E shows the difference in ultimate temperature of the thermistors of the smell generating module under different heating power levels at different heating temperature intervals according to certain embodiments of the present invention.

Turning to FIG. 2E, ultimate temperature variations of the thermistor with the B value of 4250K under different power levels during each corresponding temperature interval were measured. It can be seen that the higher the heating powers provided, the higher ultimate temperatures were resulted. This phenomenon is likely caused by the thermal inertia.

Figure 2F:
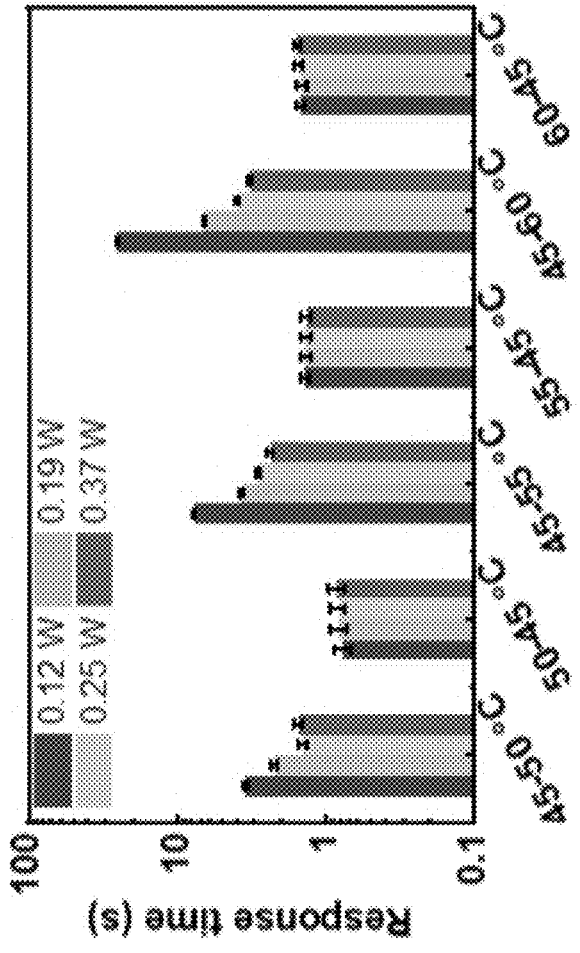
FIG. 2F shows the difference in response time of the thermistors of the smell generating module under different heating power levers at different heating temperature intervals.

Apart from analyzing the ultimate temperatures at different heating powers, the response times at the corresponding temperature intervals under different power levels were also compared, and the results are shown in FIG. 2F, in which the lowest heating power resulted in the longest response time while the highest heating power led to the best time response performance. It should be noticed that the response times in temperature-rising processes varied much more significantly than those in temperature-dropping processes. As the lumped conductive Cu coil with a DC voltage generated a single directional magnetic field, it interacted with the magnet and then produced an electromagnetic force to lift the coil up.

Figure 2G:
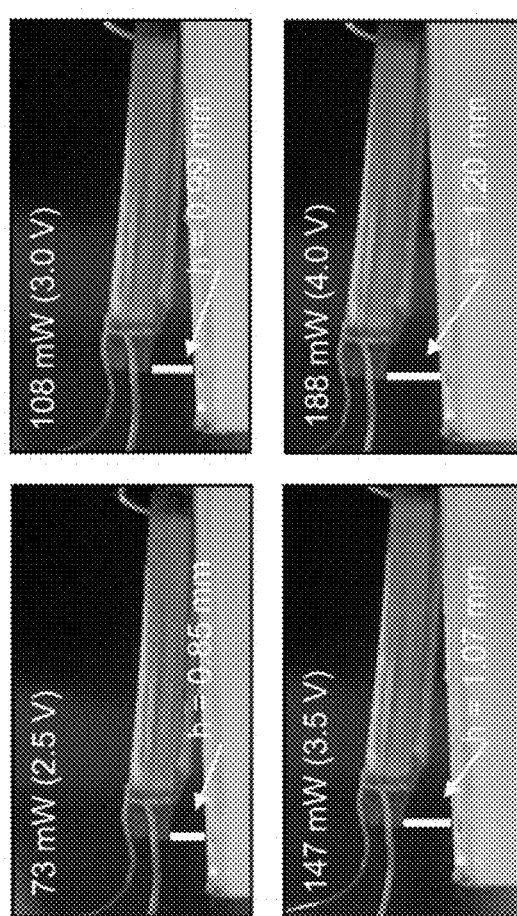
FIG. 2G shows the effect of different voltages on lifting-up height of an electrically conductive coil of the smell generating module according to certain embodiments of the present invention.
Figure 2H:
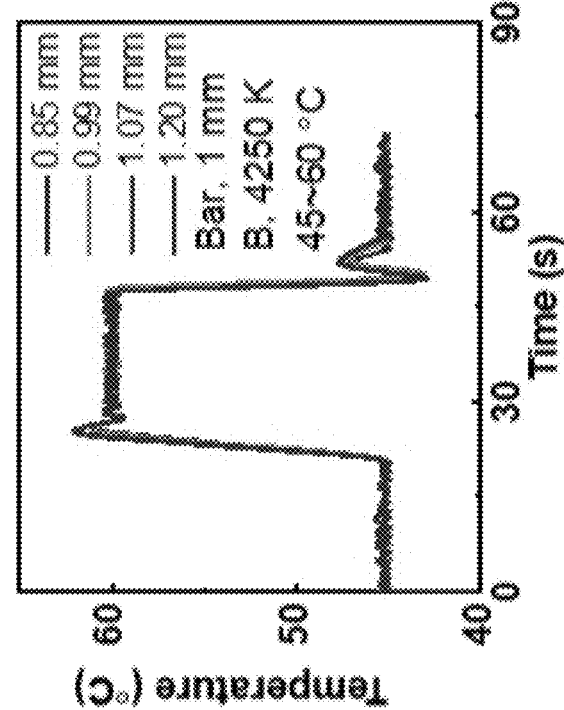
FIG. 2H shows the change in temperature of the thermistor of the smell generating module against different lifting-up heights of the electrically conductive coil according to an embodiment of the present invention.

FIGS. 2G and 2H respectively show the lifting-up heights of the Cu coils at different voltages of the heating power and the temperature change of the thermistor with a B value of 4250 K at the corresponding lifting-up height of the coil. From the results, the lifting-up height had little impact on the temperature distribution of the smell generators. Thus, it is verified that the temperature detection is not affected by the vibration operation of magnet.

Figure 2I:
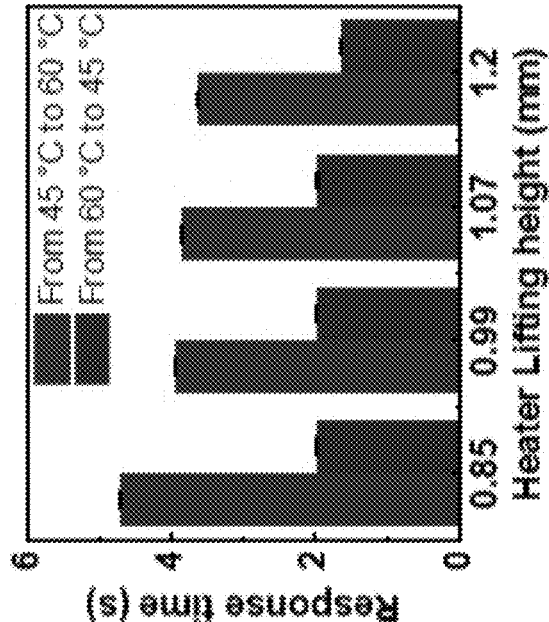
FIG. 2I shows the effect of different lifting-up heights of the electrically conductive coil on the response time of the thermistor during heating and cooling cycle according to certain embodiments of the present invention.
Figure 2J:
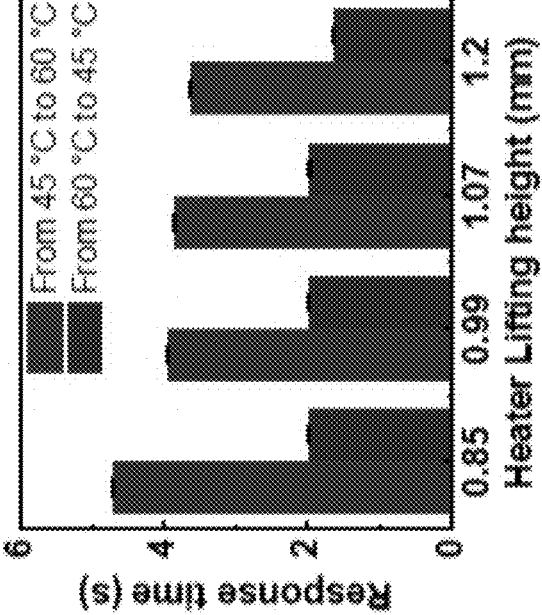
FIG. 2J shows the effect of different lifting-up heights of the electrically conductive coil.

FIG. 2I shows that the response time had only a slight variation of less than 1.5 s and did not have significant variations during both the temperature rising and dropping processes at different lifting-up heights of Cu coil. Besides, FIG. 2J shows that almost no variations in ultimate temperatures under different lifting-up heights of Cu coil were observed.

Figure 2K:
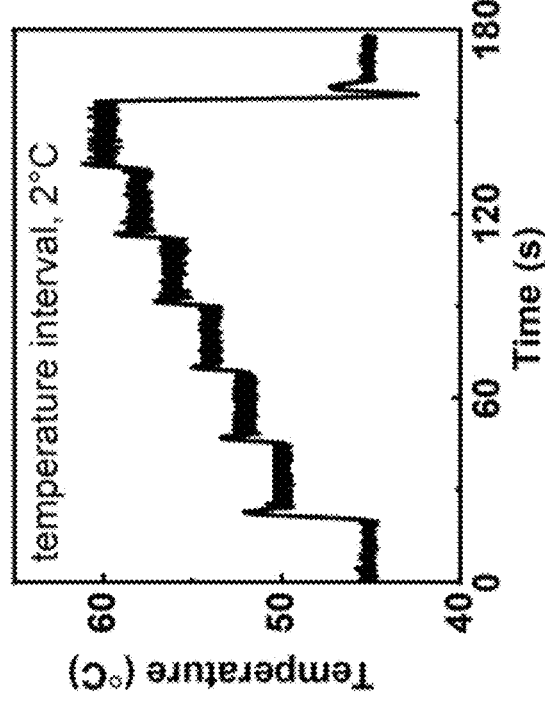
FIG. 2K shows the change in temperature with a rising temperature of the thermistor of the smell generating module at a constant temperature interval according to certain embodiments of the present invention.

FIG. 2K shows the temperature change of the thermistor with the temperature rising interval of 2° C. over time, where the results suggest that the temperature of the thermistor is consistent with the rising temperature with an interval of 2° C.

Figure 2L:
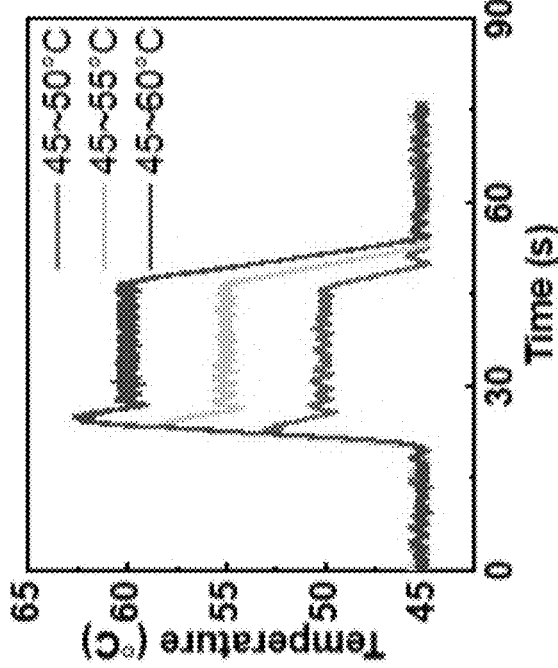
FIG. 2L shows the change in temperature with different heating temperatures applied on the thermistor of the smell generating module and without cooling after heating according to certain embodiments of the present invention.
Figure 2M:
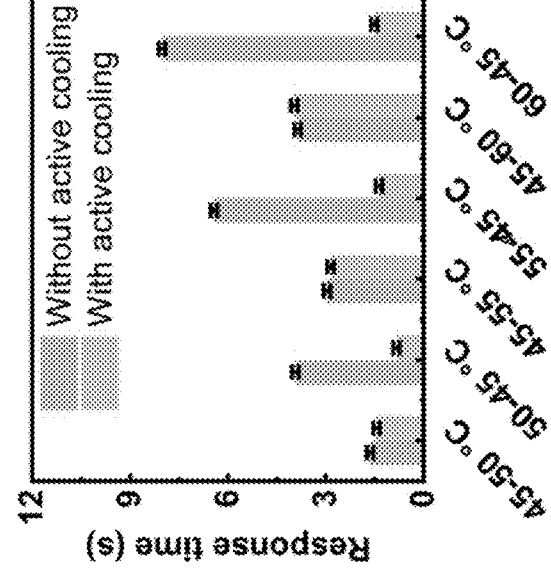
FIG. 2M shows the effect of cooling on response time of the thermistor of the smell generating module after heating at different temperatures according to certain embodiments of the present invention.

FIG. 2L shows the temperature curves over time by increasing the temperature from 45° C. to 50° C., 55° C., 60° C. and dropping to 45° C. without active cooling, respectively. In order to compare the effects between without active cooling and with active cooling, the response times at each temperature interval with or without active cooling were measured, and the results are shown in FIG. 2M. It can be observed that there are no obvious variations in the response time during the temperature rising process while there are obvious variations during the cooling process. With the help of active cooling, the temperatures could be decreased with a quick response time of less than 1.5 s until reaching the stabilized temperature.

Figures 3A, 3B:
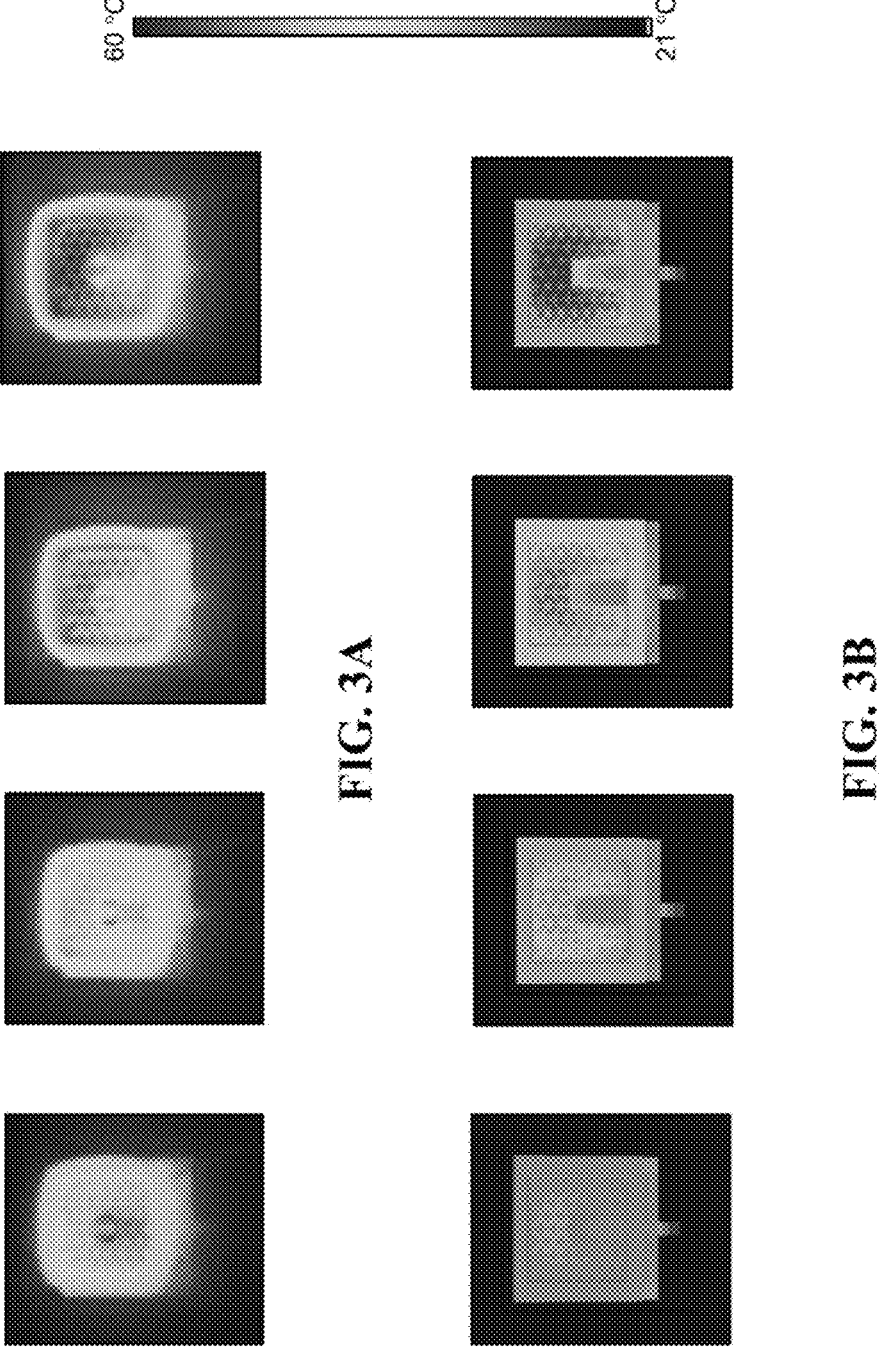
FIG. 3A shows infrared thermographic maps of the smell generating module according to certain embodiments of the present invention heated at different temperatures.
FIG. 3B shows thermal field distributions of the smell generating module according to certain embodiments of the present invention heated at different temperatures.

The smell generator 106 was also subject to a number of stability tests under the influences of long-term heating and cooling cycles or different vibration amplitudes of the conductive coil, and the results are shown in FIGS. 3A to 3F, respectively. FIGS. 3A and 3B show the thermographic maps and thermal field distributions of the smell generator having a thermistor with a B value of 4250 K, respectively. The thermal field distributions as shown in FIG. 3B are well-matched with the thermographic maps as shown in FIG. 3A, which verifies that the Au heating channel can work effectively and reach up to the required temperatures.

Figure 3C:
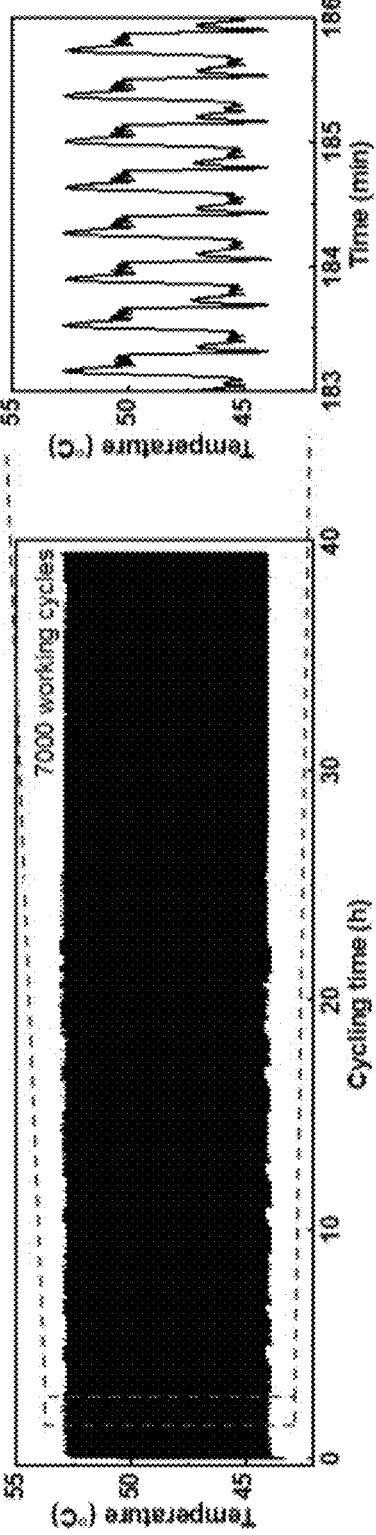
FIG. 3C shows the change in temperature of the smell generating module according to certain embodiments of the present invention over 7000 heating and cooling cycles.

The long-term stability of the smell generator 106 was subject to over 7000 heating and cooling cycles, and the temperature variations over the 7000 working cycles are shown in FIG. 3C. From FIG. 3C, it can be observed that the temperatures change pattern was kept at a very stable level without any sudden variations or distortions even after 7000 working cycles. Right panel in FIG. 3C is an enlarged view of the temperature curve of the smell generator 106 after 3-hour working cycles. After the 3-hour working cycles, the heating channel of the smell generator 106 could be repeatedly heated and cooled effectively, and the temperatures were detected normally with high accuracy, demonstrating the feasibility and durability of the smell generator 106.

Figure 3D:
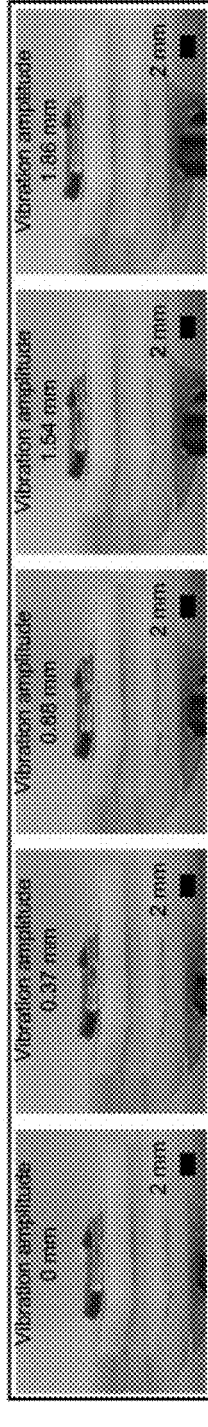
FIG. 3D shows the effect of vibration of the electrically conductive coil on the temperature distributions of the smell generating module according to certain embodiments of the present invention.
Figure 3E:
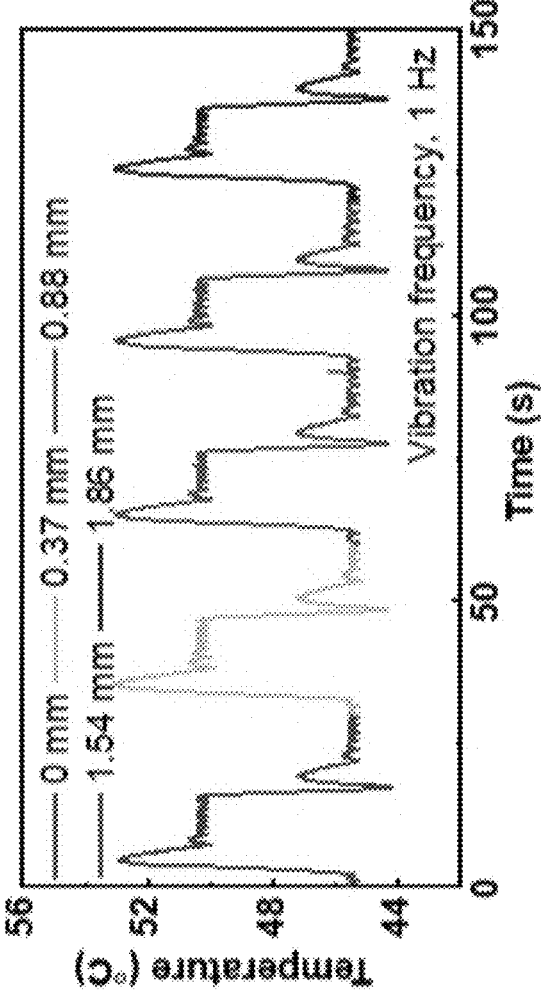
FIG. 3E shows the change in temperature of the smell generating module against different vibration amplitudes of the electrically conductive coil according to certain embodiments of the present invention.

In order to check the effects of the vibration of the coil on the temperature distributions, the temperature change of the conductive coil of the smell generator under different vibration amplitudes was recorded, and the results are shown in FIGS. 3D and 3E. FIG. 3D shows a series of optical images of the conductive coil of the smell generator 106 under different vibration amplitudes of 0 mm, 0.37 mm, 0.88 mm, 1.54 mm and 1.86 mm. FIG. 3E shows the temperature curve over time when the conductive coil vibrates at different vibration amplitudes, where different colors represent different vibration amplitudes. It can be concluded that different vibration amplitudes under 1.86 mm will not affect the electric heater's normal working, as well as the temperature detections.

Figure 3F:
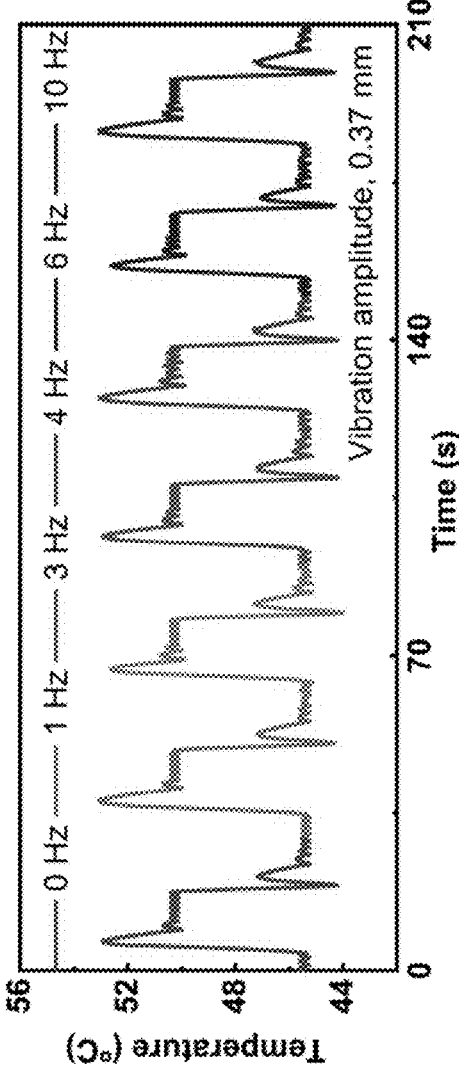
FIG. 3F shows the change in temperature of the smell generating module against different vibration frequencies of the electrically conductive coil.

Furthermore, the temperatures at different vibration frequencies under the vibration amplitude of 0.37 mm were measured, and the results are shown in FIG. 3F. It can be observed that the vibration frequency also will not affect the electric heater's normal working, as well as the temperature detections.

Therefore, the various test results verify that the present invention works properly with sufficient accuracy, flexibility, feasibility, stability and durability.

Figure 4A:
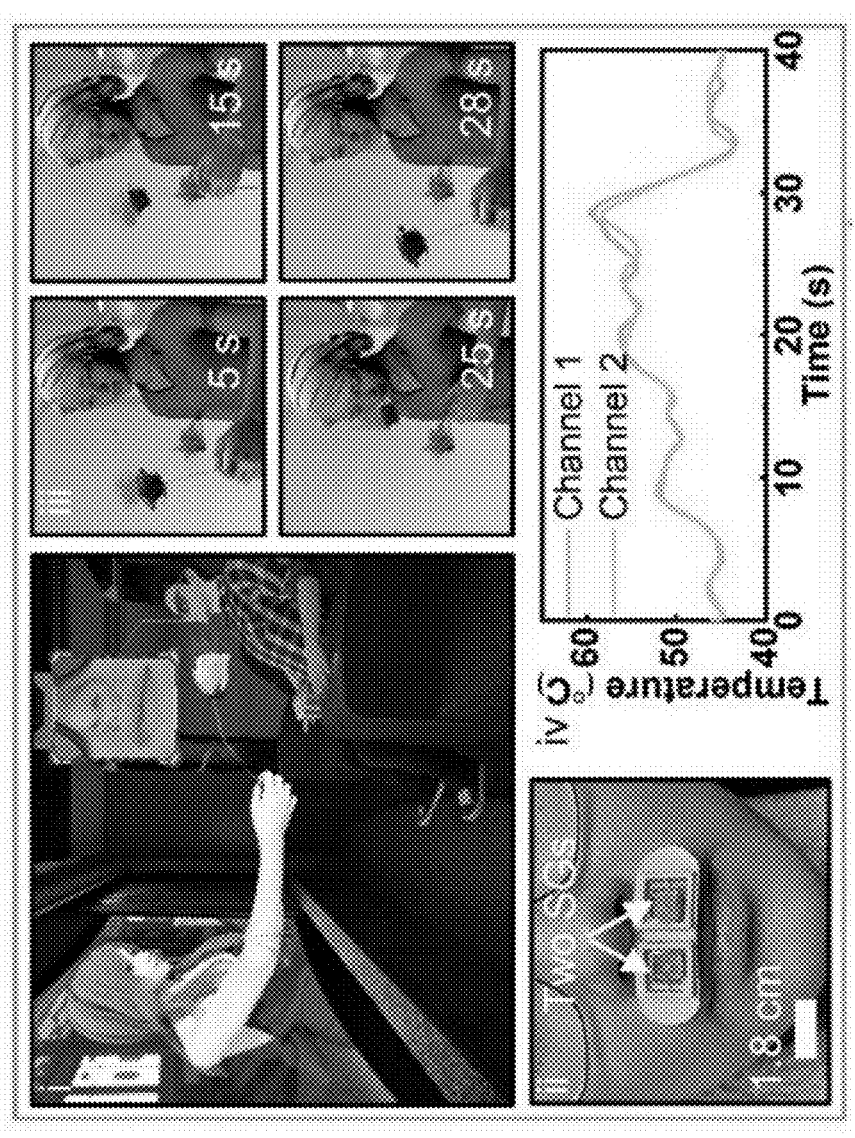
FIG. 4A depicts a first example of using the present device in immersive environments according to certain embodiments of the present invention.
Figure 4B:
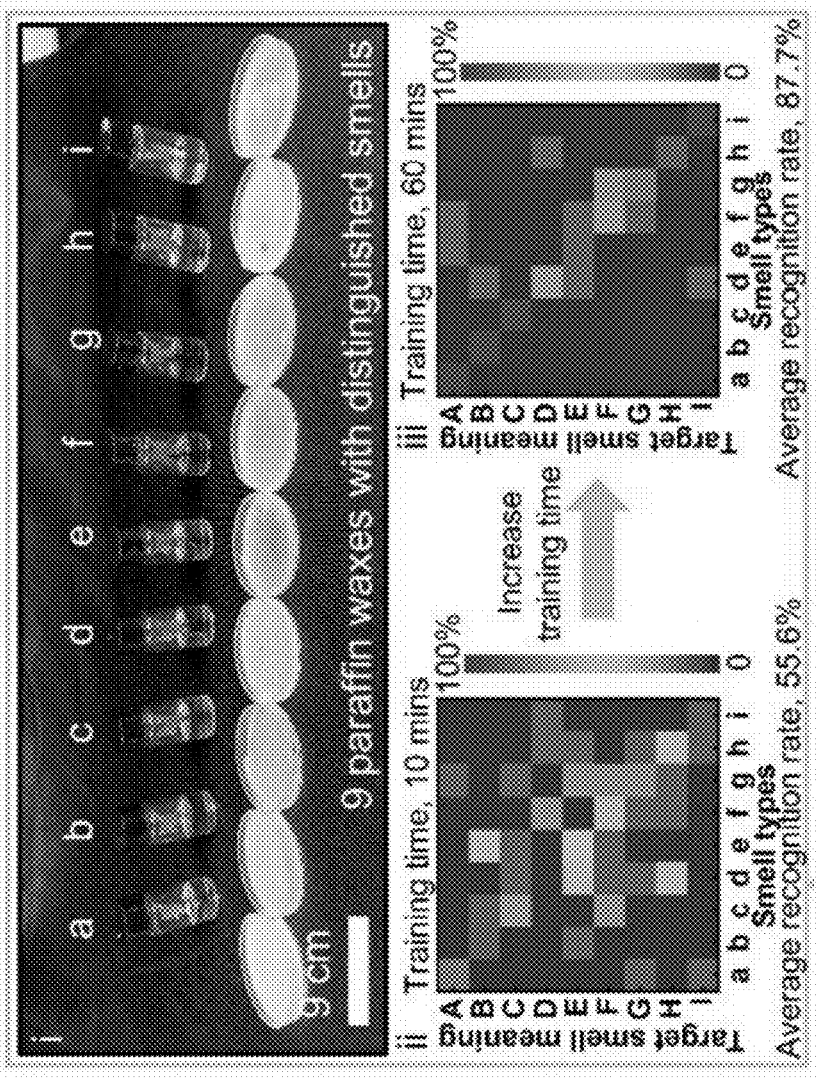
FIG. 4B depicts a second example of using the present device in assisting communication of a person in the absence of visual and audio senses according to certain embodiments of the present invention.
Figure 4C:
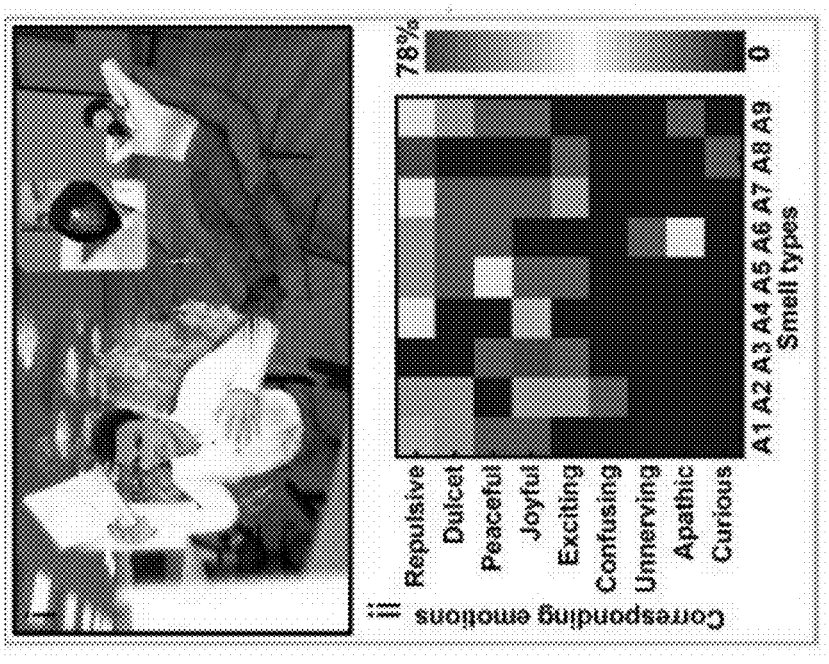
FIG. 4C depicts a third example of using the present device in affecting human emotions according to certain embodiments of the present invention.
Figure 4D:
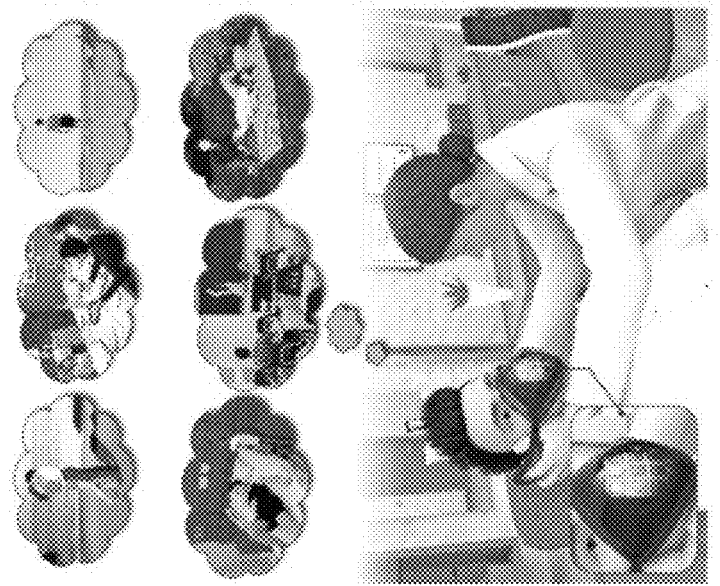
FIG. 4D depicts a fourth example of using the present device in medical treatment for amnesia according to certain embodiments of the present invention.
Figure 4E:
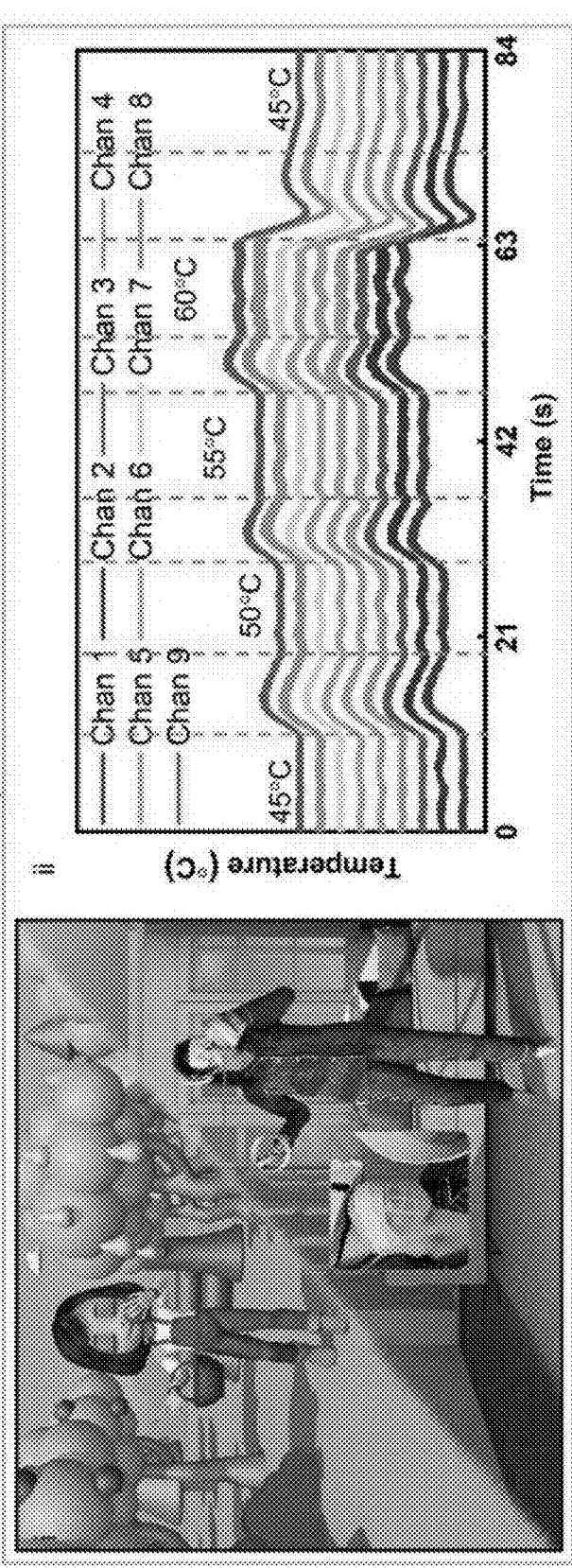
FIG. 4E depicts a fifth example of using the present device in a virtual immersive environment according to certain embodiments of the present invention.

FIGS. 4A to 4E schematically depict five examples of potential applications of the present device, including four-dimension movie watching (FIG. 4A), medical instruments (FIG. 4B), human emotion controlling (FIG. 4C), healthcare (FIG. 4D), and virtual/augmented reality (VR/AR) in consumer electronics (FIG. 4E).

In FIG. 4A, it shows the present device with two smell generators for providing an immersive experience for users when they are watching movies with smell feedback. As shown in insets (iii) and (iv), smart electronics could be used to wirelessly control the temperature of the heating elements in the smell generators for yielding the corresponding odors with controllable production rate.

In FIG. 4B, different odors generated by the present device can be used for delivering messages, which could help a person without hearing and vision or relying on olfaction to communicate with others. As a result, an average recognition rate for users wearing the present device having multiple smell generators with nine distinguished odors generated could reach up to 87.7% after training the users to be familiar with those odors for about an hour.

In FIG. 4C, the emotion response of ten volunteers after being subject to nine different odors by attaching the present device on their skin for about 3 secs was studied by conducting a qualitative survey to record presence or absence of nine common human emotions after being subject to each of the nine odors. As shown in inset (ii), the possibility where the ten volunteers could become happier after smelling sweet orange flavor (sample A3) could reach up to about 78%, which demonstrates that present device has a great potential in controlling human emotions.

In FIG. 4D, it shows a use of the present device in the medical treatment for amnesia in a patient wearing a face mask incorporating the present device with nine different odors generated from the corresponding smell generators. By sensing a specific odor, the patient could be induced to memorize some scenarios barely remembered related to the corresponding smell.

In FIG. 4E, it shows a VR application of the present device when a user wearing the corresponding electronics is provided with various odors in a virtual visual surrounding, e.g., walking in a garden. Inset (ii) presents the electrical response of nine different smell generators working at the same time. The temperature variation patterns among the nine smell generators are substantially identical.

Figure 5:
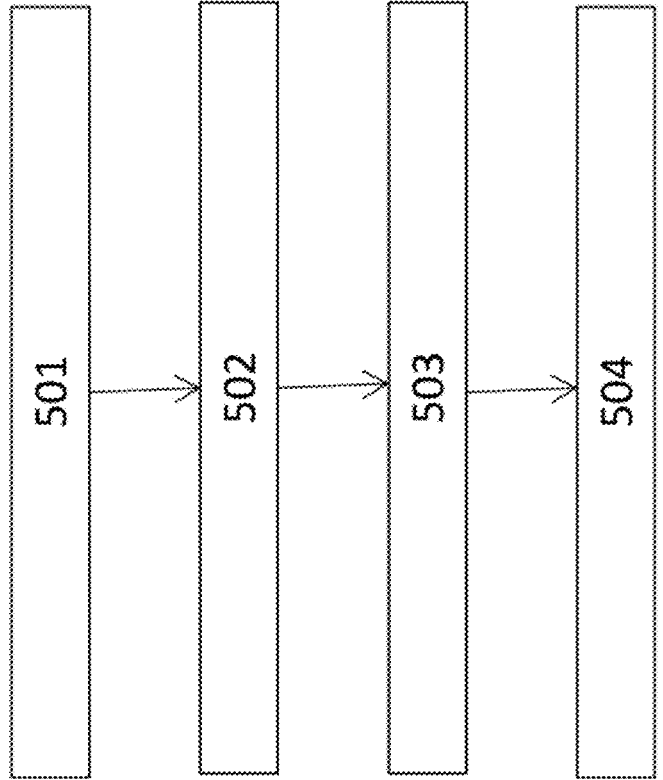
FIG. 5 is a flowchart depicting a method for generating olfaction to a user of the present device in an immersive environment according to certain embodiments of the present invention.

Turning to FIG. 5, a simplified flowchart illustrating an example of applying the present device with a device or system of providing immersive environments for a user thereof is provided. Initially, the present device is attached on any part of the user's skin 501. In this example, the user is provided with a device or system capable of providing various immersion senses in a virtual environment together with a software to assist the execution of different instructions from the user, analyze the data received by different devices and translate the same into various outputs such as visual, audio and olfactory senses. The device capable of providing various immersion senses in a virtual environment includes any portable or wearable VR, AR and MR devices, and such a device can serve as a master control device of the present smell generating device. After attaching the present device to the user's skin, the present device is connected to the master control device wirelessly 502. The user may activate the smell generating device through an instruction sent by the master control device 503, or alternatively through any wireless or physical control/switch of the smell generating device, in order to elevate the temperature of the heating element to evaporate odorants in the odorant chamber. The odorant is preferably a phase change material incorporated with one or more of scent- or odor-releasing source, or an inhalable content. Once the chamber is heated to a temperature above the melting temperature of the phase change material, the corresponding scent, odor or inhalable content will be released through an open channel of the smell generating module to the surroundings. Upon receipt of a deactivation instruction, the chamber and the heated source are actively cooled down to a temperature below the melting temperature of the phase change material through a corresponding electromagnetic actuation mechanism so as to cease the release of scent, odor or inhalable content from the chamber 504. It should be understood that the sequence of the steps described in this example can be changed according to the needs of the user. For example, the smell generating device can be connected to the VR/AR/MR device wirelessly prior to attachment onto the user's skin.

In some other examples, the smell generators may be used for releasing other odors than the original odors. In those cases, the smell generators are able to support replacement of a new odorant in a few simple steps by the user. When replacement of the odorant is needed, the user can first activate the heating element of the smell generator to increase the temperature of the chamber housing the odorant, e.g., paraffin wax, to above the melting temperature of the phase change material contained therein. The molten state of the phase change material can then be removed by cotton or alike. No separate component such as cartilage for carrying the new odorant is required to replace the old/used odorant in the present device. This can prevent the heating elements such as the heating electrode under the chamber from potential damage by repeated mechanical replacements, or be absent of any complicated mechanical design for advancing the replacement. After removal of the old/used odorant from the chamber, the user may simply add the new odorant into the chamber while the heating elements thereunder are stabilized at the temperature above the melting temperature of the phase change material inside to allow the user to formulate a desirable odor-releasing element at its molten state. The user can also test the evaporation of the newly formulated odor-releasing element when the chamber is still maintained at the stabilized temperature. In case of replacing the old paraffin wax with a new batch of paraffin wax, the stabilized temperature is preferably at about 60 degree Celsius. Once the odorant is replaced and the new odor may be tested, the active cooling element can be activated to quickly cool down the temperature of the chamber, thereby solidifying the odorant.

Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

The present invention has the following advantages over the conventional VR devices: skin integration, flexibility, disposability, human-machine interaction. Like other wearable VR devices (especially those which generate odors), the potential applications of the present invention include, but not limited to: immersive human-computer interaction experience (e.g., movies, games, etc.) in any entertainment environment including movie theaters, amusement arcades, etc.; auxiliary medical equipment (e.g., aromatherapy) in clinical and corporate sites.

In terms of implementing the present invention in virtual immersive environments, one possible way is to add an olfactory display to VR which could enhance immersion sense of users in a virtual environment, and a precise control of smell would facilitate a more realistic experience for users. These kinds of flexible odor generators can be integrated into visual virtual reality systems and be driven using a modified version of existing software, thus allowing the options of immersive environments with synchronizing (or unsynchronizing) visual and olfactory VR. Such a device, as a complement to the mass audio-visual entertainment experience, such as film, television, and games, could be used in entertainment premises such as movie theaters and amusement arcades. Besides, in high-risk industries such as defense, fire protection, oil and gas, and aviation, incorporating olfactory perception into virtual reality technology can enhance situational realism and facilitate hazard identification analysis, thereby reducing financial losses and adverse health outcomes.

Other applications include olfactory-driven training and therapy by selectively providing specific odors or inhalable content that is capable of altering emotional state or exert a positive effect on relieving stress and improving mental relaxation.

The present invention is also applicable as aromatherapy in combination with VR therapy to treat psychological disorder such as depression and phobia and improve the immune function of patients. Some emotion-influent odors, such as citrus fragrance, orange, lavender, and green odor from oak leaves, could be used in the present invention to reduce stress and promote relaxation and pleasantness in both clinical and corporate settings.

What is claimed is:

1. A flexible smell generating device for use on human skin comprising a multi-layered structure, the multi-layered structure comprising:
   one or more smell generating modules;
   one or more active cooling elements;
   a plurality of electronic circuits; and
   a substrate,
   wherein each of the one or more smell generating modules comprises at least one open channel and at least one chamber containing at least one phase change material incorporating one or more items selected from a scent-releasing substance, plural odorants and an inhalable content,
   wherein an individual active cooling element of the one or more active cooling elements is controlled by a corresponding electronic circuit and is configured to actively cool a corresponding smell generating module upon activation by the corresponding electronic circuit, wherein the individual active cooling element comprises at least one electrically conductive coil and a magnet, wherein the at least one electrically conductive coil is placed around the corresponding smell generating module, and wherein the at least one electrically conductive coil and the magnet are configured such that when the at least one electrically conductive coil is powered off by the corresponding electronic circuit, the at least one electrically conductive coil falls due to gravity and contacts with the magnet to thereby conduct heat from the corresponding smell generating module to the magnet and cease release of odors from the corresponding smell generating module,
   wherein the substrate is arranged to be disposed as a most proximal layer to the human skin and is configured to secure the multi-layered structure to the human skin, and
   wherein the substrate is flexible and adhesive for securing the multi-layered structure to the human skin and is configured to cause the flexible smell generating device to be flexible.

2. The flexible smell generating device of claim 1, wherein each of the smell generating modules further comprises at least one heating element for heating the at least one phase change material, and at least one temperature sensing and control element for sensing and controlling temperature variations of the smell generating module during said heating.

3. The flexible smell generating device of claim 2, wherein the at least one heating element is a pair of serpentine-shaped electrodes.

4. The flexible smell generating device of claim 2, wherein a pair of serpentine-shaped electrodes is made of a metal selected from gold, chromium, and copper.

5. The flexible smell generating device of claim 2, wherein the at least one temperature sensing and control element is a thermistor.

6. The flexible smell generating device of claim 1, wherein the at least one phase change material comprises paraffin wax.

7. The flexible smell generating device of claim 1, wherein the magnet is positioned within a magnetic field generated by the at least one electrically conductive coil when an electric current is applied to the at least one electrically conductive coil.

8. The flexible smell generating device of claim 7, wherein each of the smell generating modules further comprises a first polymer layer having a cavity and a second polymer layer having a switch.

9. The flexible smell generating device of claim 8, wherein the magnet is disposed within the cavity of the first polymer layer while the at least one electrically conductive coil is attached to the switch of the second polymer layer.

10. The flexible smell generating device of claim 9, wherein the plurality of electronic circuits comprises a microcontroller unit configured to control open and close of the switch in order to control the electric current flowing through the at least one electrically conductive coil, thereby adjusting an oscillating frequency and amplitude thereof.

11. The flexible smell generating device of claim 9, wherein the first polymer layer is made of polyethylene terephthalate and the cavity is defined by a polydimethylsiloxane ring disposed on the first polymer layer.

12. The flexible smell generating device of claim 9, wherein the second polymer layer is made of polyimide and the switch is a cantilever.

13. The flexible smell generating device of claim 7, wherein the at least one electrically conductive coil is made of a metal selected from copper, silver and gold.

14. The flexible smell generative device of claim 1, wherein the multi-layered structure further comprises a plurality of electrical outputs each communicating with the corresponding smell generating module individually to provide the corresponding smell generating module with an electric current at a switching frequency.

*    *    *    *    *